United States Patent
Berntsen et al.

(10) Patent No.: US 10,557,113 B2
(45) Date of Patent: Feb. 11, 2020

(54) SURFACE DETECTION AND PICKTOOL MANIPULATOR

(71) Applicant: BD KIESTRA B.V., Drachten (NL)

(72) Inventors: Martijn Xander Berntsen, Leeuwarden (NL); Jurjen Sinnema, Joure (NL); Martijn Kleefstra, Surhuisterveen (NL)

(73) Assignee: BD KIESTRA B.V., Drachten (NL)

( * ) Notice: Subject to any disclaimer, the term of this patent is extended or adjusted under 35 U.S.C. 154(b) by 218 days.

(21) Appl. No.: 15/560,048

(22) PCT Filed: Mar. 30, 2016

(86) PCT No.: PCT/EP2016/056910
§ 371 (c)(1),
(2) Date: Sep. 20, 2017

(87) PCT Pub. No.: WO2016/156390
PCT Pub. Date: Oct. 6, 2016

(65) Prior Publication Data
US 2018/0072982 A1    Mar. 15, 2018

Related U.S. Application Data

(60) Provisional application No. 62/140,002, filed on Mar. 30, 2015.

(51) Int. Cl.
*C12M 1/00* (2006.01)
*C12M 1/36* (2006.01)
(Continued)

(52) U.S. Cl.
CPC ............ *C12M 47/02* (2013.01); *C12M 33/04* (2013.01); *C12M 41/48* (2013.01); *C12N 1/02* (2013.01);
(Continued)

(58) Field of Classification Search
None
See application file for complete search history.

(56) References Cited

U.S. PATENT DOCUMENTS 9,091,672 B2    7/2015 Wilmes
9,677,044 B2    6/2017 Botma et al.
(Continued)

FOREIGN PATENT DOCUMENTS

CN    103097511 A    5/2013
CN    103958661 A    7/2014
(Continued)

OTHER PUBLICATIONS

Chinese First Office Action and Search Report issued in corresponding CN application 2016800183921 dated Jun. 24, 2019.
(Continued)

*Primary Examiner* — Kathryn Wright
(74) *Attorney, Agent, or Firm* — Botos Churchill IP Law LLP

(57) ABSTRACT

A picktool manipulator device collects a specimen from a culture medium. In a first mode of operation, a picktool is allowed to move in an axial direction relative to support structure of the device. A detector may generate a signal in response to movement of the body in the axial direction so as to determine a height at which the picktool contacts the medium. The device may operate in the first mode when collecting a specimen from a culture medium. A second mode of operation constrains or precludes axial movement of the picktool. In some cases, the device may operate in the second mode when receiving a new picktool or discarding a used picktool.

16 Claims, 10 Drawing Sheets

(51) Int. Cl.
*C12N 1/02* (2006.01)
*C12Q 1/24* (2006.01)
*G01N 35/00* (2006.01)
*G01N 35/10* (2006.01)
*C12M 1/26* (2006.01)

(52) U.S. Cl.
CPC ........... *C12Q 1/24* (2013.01); *G01N 35/0099* (2013.01); *G01N 35/10* (2013.01)

(56) References Cited

U.S. PATENT DOCUMENTS

| | | | |
|---|---|---|---|
| 10,144,948 B2 | 12/2018 | Charrier et al. | |
| 2008/0274537 A1* | 11/2008 | Bornmann | B01L 3/0279 435/285.1 |
| 2012/0227471 A1* | 9/2012 | Smith | G01N 35/1011 73/61.59 |
| 2013/0109047 A1 | 5/2013 | Charrier et al. | |
| 2014/0271405 A1 | 9/2014 | Wilmes | |
| 2014/0322745 A1 | 10/2014 | Decaux et al. | |

FOREIGN PATENT DOCUMENTS

| | | |
|---|---|---|
| CN | 104049092 A | 9/2014 |
| EP | 2574660 A1 | 4/2013 |
| EP | 2778688 A1 | 9/2014 |
| EP | 2793031 A1 | 10/2014 |
| JP | 2013531505 A | 8/2013 |

OTHER PUBLICATIONS

Notice of Reason for Refusal issued in corresponding JP application No. 2017-551041 dated Oct. 16, 2018.
International Search Report from PCT Application No. PCT/EP2016/056910 dated Jun. 21, 2016.

* cited by examiner

SURFACE DETECTION AND PICKTOOL MANIPULATOR

CROSS-REFERENCES TO RELATED APPLICATIONS

The present application is a national phase entry under 35 U.S.C. § 371 of International Application No. PCT/EP2016/056910 filed Mar. 30, 2016, published in English, which claims priority from U.S. Provisional Application No. 62/140,002, filed Mar. 30, 2015, all of which are incorporated herein by reference.

BACKGROUND OF THE INVENTION

The subject matter of the present application relates to robotic manipulator equipment and methods of operating the same. In one example, robotic manipulator equipment may be used for collection of a specimen from a culture medium such as an agar plate.

For collecting a specimen using a robotic system, e.g., for collecting a specimen of a microbial or bacterial culture from a viscous culture medium such as, for example, an agar plate, it is necessary that the robotic system accurately positions itself for collection of the specimen. Position of the culture in a horizontal plane (e.g., the positions in x and y horizontal directions in a Cartesian coordinate space) can be determined through calculations based on an imaging system. However, such imaging system cannot determine the vertical position of the culture with enough accuracy. The vertical position can be difficult to determine with an imaging system because the specimen and the medium may each vary greatly in characteristics such as, but not limited to, color, transparency, reflectance and moisture content.

Several methods have been proposed and investigated but no suitable solution has been found so far. Determining the vertical position of the specimen is essential because moving the robotic system too deep relative to the surface of the medium might cause the system to collect too much material of the culture medium, or collect too little of the specimen, e.g., collect too few bacteria. In either case, these problems can lead to erratic measurements and unreliable test results.

In view of these problems, further improvements in robotic collection systems and methods therefor are needed.

SUMMARY OF THE INVENTION

According to an aspect of the disclosed embodiments, described herein is a device for collecting a specimen from a culture medium. The device includes a body portion that will receive a disposable picktool. As such the body portion is configured to receive the picktool, which is easily separated from the body portion after use. The body and picktool assembly are in approximately axial alignment in the described embodiment. The device includes a detector that generates a signal in response to a force applied to the picktool when the picktool is brought into contact with either the culture medium or a specimen disposed on the culture medium.

The device is configured to operate in at least first and second modes. In the first mode, the body and picktool assembly move relatively freely in the axial direction. This direction is roughly perpendicular to the surface of the culture medium. The second mode applies more resistance to the axial movement of the body and picktool assembly than when the device is in the first mode.

The picktool is configured to operate over a predetermined range of motion. In one embodiment, the resistance to movement in the axial direction when in the second mode progressively increases with displacement of the body beyond the predetermined range of motion. In further embodiments, the amount of the resistance to movement in the second mode increases as a step function upon displacement of the body beyond the first predetermined range of motion.

In some embodiments the device has a spring configured to begin to resist axial movement of the body in response to movement of the body at or following contact between the picktool and a specimen disposed on the culture medium when the device switches to the second mode. For example, the device is configured to switch from the first mode to the second mode when the picktool is in contact with or comes into contact with the specimen disposed on the culture medium.

In some embodiments the detector is configured to generate a signal in response to detecting a relative position between the device and the specimen.

In order to switch from the first mode to the second mode, the body comprises a structure coupled to the body. The body moves more freely in the axial direction relative to the structure in the first mode and the body is either more resistant or locked from such axial movement in the axial direction in the second mode. For example, a key is provided coupled to the body. The key cooperates with an opening in the structure above the key so that the key does not engage and may advance into and through the structure in the first mode. However, in the second mode the key cannot advance into and through the structure. In further embodiments the structure includes a motor coupled to the body for rotating the body in a direction about the axis. In these embodiments the motor is configured to rotate the body relative to the structure between the first position corresponding to the first mode in which the key can advance into and through the structure and the second position corresponding to the second mode in which the key cannot advance into and through the structure. In other further embodiments the key has at least one lateral extension away from an axis common to the key and body. The structure has an opening sized to permit the at least one extension to pass there through.

In other embodiments the structure has a sleeve through which the body extends. When the device is operating in the first mode in these embodiments the body is freely moveable in the axial direction within the sleeve and the sleeve restrains the body in coaxial arrangement therewith. When operating in the second mode the sleeve and structure cooperate to restrain movement of the body relative to the structure.

In alternative embodiments the device that collects the specimen from the culture medium has a body that receives and retains a removable picktool. The picktool extends from the device when received by the body. The device has a mechanism for moving the body (which can be coupled with the picktool) in Cartesian space. Therefore, the picktool can be moved from a first location where it is received by the device to a second location where it is used to pick a specimen disposed on a culture medium. The device includes a mechanism that advances the picktool to the specimen. The device also includes a signal generator that generates a signal when the picktool is advanced into contact with the specimen disposed on the culture medium. The device includes a mechanism that allows the body to move more freely in a direction proximately perpendicular to the surface of the culture medium within a predetermined range of motion in a first mode. The mechanism, when switched to a second mode, increases the resistance of the body to movement in the proximately perpendicular direction when the body travels beyond the predetermined range of motion in a second mode. In certain embodiments the body moves freely in the about perpendicular direction (with respect to the culture media) in the first mode and does not move in the about perpendicular direction in the second mode.

According to another aspect of the disclosure, a method for collecting a specimen from a culture medium is disclosed. The method may include initiating a first mode of a device for collecting a specimen from a culture medium, the first mode permitting movement of the device in an axial direction relative to a support structure of the device; moving the device in the axial direction to receive and retain a picktool configured to collect the specimen; moving the picktool, by the device, into contact with the specimen disposed on the culture medium; initiating a second mode of the device and precluding movement of the device in the axial direction; manipulating the picktool while the picktool is attached to the device to collect the specimen; and depositing the collected specimen at a collection location.

In one embodiment of this aspect, the step of manipulating may include the device rotating the picktool. The picktool can additionally or alternatively be released from the device so as to discard the picktool.

In some embodiments, after depositing the collected specimen, the collected specimen may be processed. The step of processing may include at least one of the processes selected from the group comprising processing testing, culturing, or preserving.

In another embodiment, the method can further include detecting contact between the picktool and the culture medium. Additionally or alternatively, the method may include detecting a height at which the picktool contacts the culture movement.

DETAILED DESCRIPTION

Figure 1:
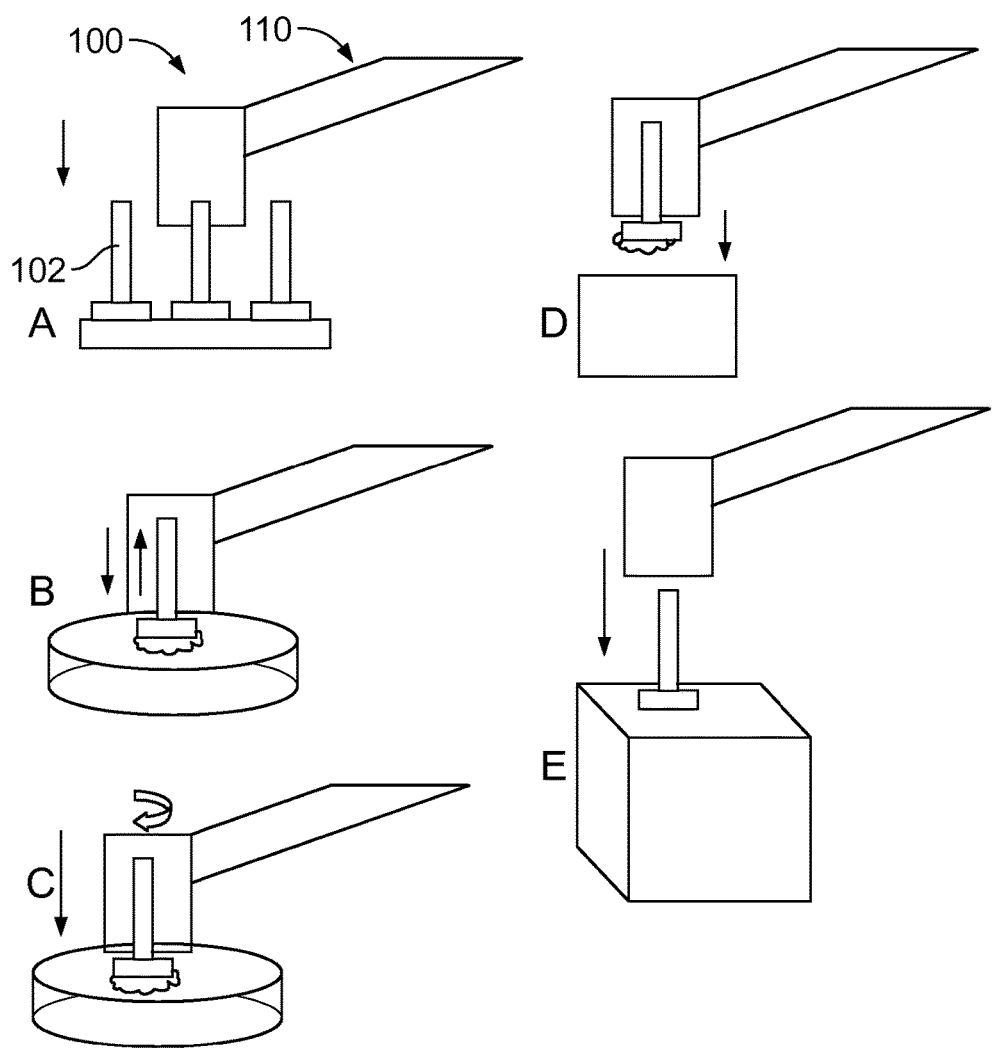
FIG. 1 is a schematic diagram illustrating movement of a device used in collecting a specimen from a medium in accordance with an embodiment of the invention.

Accordingly, a device provided herein that may be used both to detect a surface of a medium such as a surface of a specimen thereon, e.g., bacterial colony on a surface of a culture medium, e.g., an agar plate. Such device, which may also function as a rotational manipulator, and may include sensors, may also fulfill additional required functions such as detecting the presence of a replaceable picktool and receiving an unused picktool, depositing a collected specimen after collecting it, and assisting in the removal of the used picktool.

Accordingly, an improved device and method is provided for handling a picktool such as used in collecting a specimen from a medium, for example, a culture or tissue growing or otherwise supported on a medium, e.g., an agar plate. With such device, the height of the picktool relative to the medium can be accurately gauged using a signal generated by the device in response to the device moving the picktool into contact with the medium.

Thus, in one embodiment, the device can have a picktool-receiving body that receives and retains the picktool. The device may have a first mode of operation in which the body (and the picktool received thereby) moves more freely in axial directions of the body relative to a support structure of the device, such movement occurring in response to the picktool coming in contact with a medium or "engaging" the medium. When the device is moved towards the medium, typically in a downward direction or a direction that includes a substantial downward component, the picktool approaches the medium and contacts the medium while the device is moving toward the medium. As a result of such motion, the medium provides resistance to the downward motion of the picktool and the picktool-receiving body in an axial direction of the body away from the medium relative to other structure of the device, such as a support of the device. Thus, in one example, movement of the device downwardly towards the medium so that the picktool engages the medium causes the picktool and the picktool-receiving body to be urged in the axial direction, e.g., upwardly away from the medium relative to the other structure of the device.

Based on the axial movement of the body relative to the device's structure, a detector associated with the device generates a signal which can be used to determine a height of the device at which the picktool contacts the medium. The determined height is a vertical position of the device at which the device is positioned correctly for manipulating the picktool to collect a specimen from the medium. The device can then be used to collect a specimen from the culture medium. In particular examples, as described relative to FIGS. 5-10 below, the device may have structure which applies increased downforce (or increased resistance to the upward force) between the picktool and the medium to assist in the collection of the specimen from the medium.

In one embodiment, when the device reaches the previously determined height for collecting a specimen, the body is restrained from being pushed upward relative to the device structure. The device can then manipulate the picktool to collect a specimen from the medium, such as by rotating the picktool, for example, using a motor. For example, the picktool can be moved by the device relative to the medium so as to gather material of the specimen from the culture medium. In a specific example, a motor coupled to the body can rotate the picktool relative to the medium, to cause the picktool to gather specimen material from the medium. In a particular example, the material gathered from the specimen lodges on a blade or other collecting surface of the picktool.

In a second mode of operation, rather than permitting the picktool receiving body to move freely, the picktool-receiving body is restrained from or precluded from moving axially relative to the device structure. In one example of operation in this mode, the device can be operated in this second mode when receiving a new picktool or discarding a used picktool.

Figure 2:
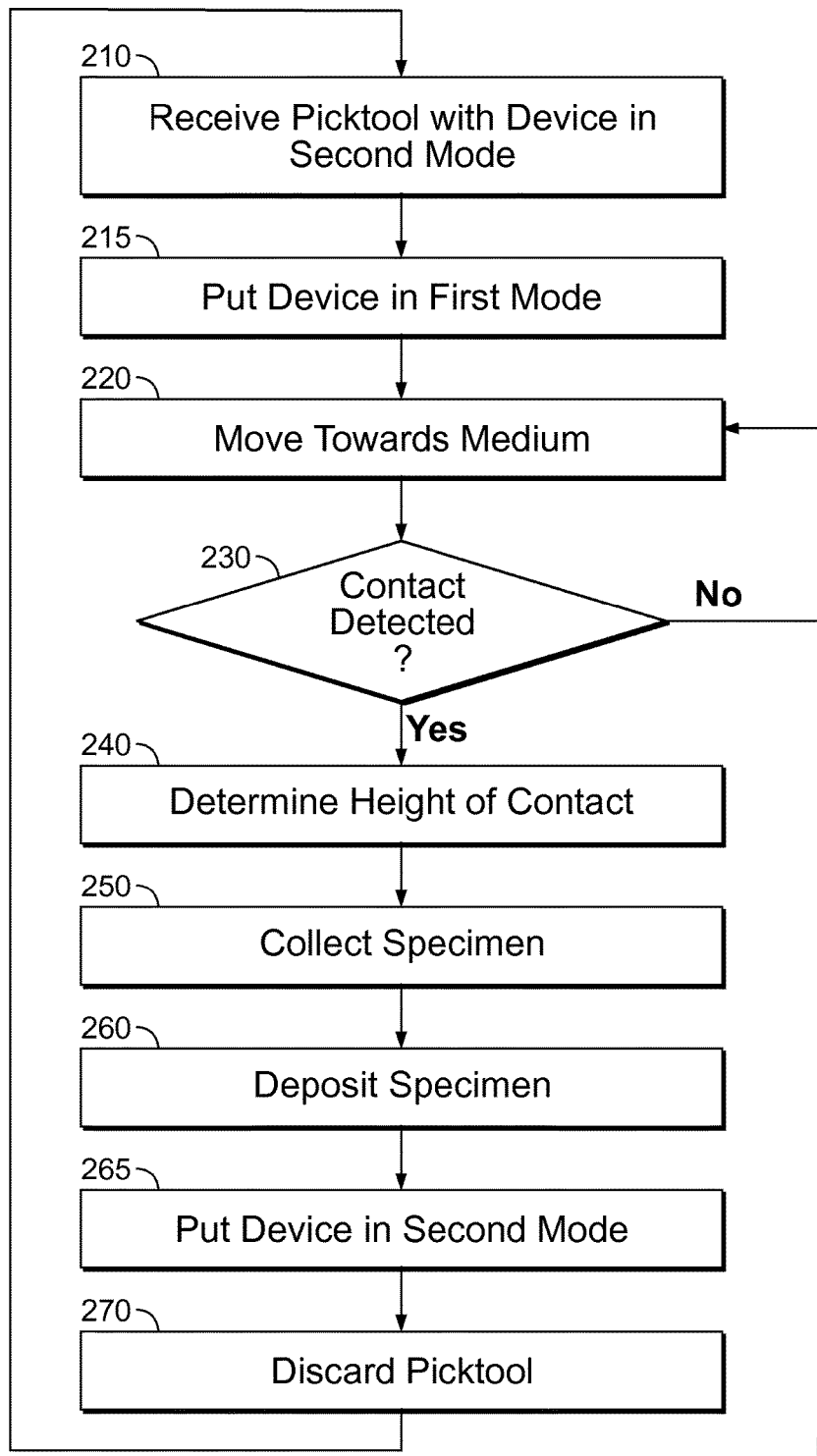
FIG. 2 is a flowchart illustrating a method of detecting a height of contact with a medium and collecting a specimen from the medium in accordance with an embodiment of the invention.

Referring now to FIGS. 1 and 2, an example is provided of using the device in an automated method to collect individual specimens at a high repetition rate suitable for use in a high volume apparatus for sample collection from an inventory of culture plates. The media can vary from plate to plate and the number and type of media can vary widely. There may be one or more picks per plate. After collecting a specimen using a picktool retained by the device, the device deposits the collected specimen at a collection location for further processing, e.g. testing, further culturing, or preservation of the specimen. Thereafter, the device can discard the used picktool and then begin the same collection process again with the receiving of another picktool, and then collecting another specimen by a method as described above either from the same plate or a different plate as required by the system.

Thus, in an exemplary method of operation using the device 100, a quantity of picktools 102 may be arranged in an array at a first station A (FIG. 1) awaiting use. In one example, an external actuator 110 can move the device 100 in multiple degrees of freedom within a coordinate space. For example, the actuator may be programmed to automatically move the device in horizontal, vertical and/or circumferential directions between stations at which various work is performed. In this way, the actuator can move the device in at least lateral directions from station to station (e.g. the first station to collect a pick tool; second station to pick the sample; third station to deposit the picked sample, etc.), and move the device in upward and downward directions when needed. The actuator is controlled electronically by components such as logic circuitry, a set of instructions executable by a processor, or both logic circuitry and a set of executable instructions. In a particular example, the actuator is controlled by one or more programs containing instructions executed by one or more processors.

Thus, as seen at A (FIGS. 1) and 210 (FIG. 2), the device can be operated in the second mode of operation which restrains or resists or dampens upward movement of the body for carrying the picktool, and the actuator may move the device in an axial direction of the picktool-receiving body such that the body receives a picktool. For example, the device can be moved downwardly such that a shaft of the picktool is received within a cavity of the body and is firmly retained to preclude relative movement between the picktool shaft and the body.

Thereafter, the device can be put in the first operational mode which permits the body to move more freely relative to the device. Then, as seen at B (FIGS. 1) and 220 (FIG. 2), the actuator may move the device in a direction, e.g., downwardly, towards a medium while the device is operated in a first mode to determine a height at which the picktool contacts the medium. The device continues to move downward so long as contact between the picktool and the sample has not yet been detected, as seen at 230 (FIG. 2). The height is determined at which a detector of the device detects contact between the picktool and the culture medium. In one example, contact is detected by detecting resistance to movement in the downward direction which translates to movement of the picktool in the upward direction.

Then, as seen at C (FIGS. 1) and 250 (FIG. 2), with the device still in the first mode of operation the picktool contacts the specimen disposed on the medium at which time the device switches from the first mode to the second mode to collect the specimen. When collecting the specimen, the device at least resists or dampens upward motion but may, in alternative embodiments, apply increased downward force to the picktool to cause the picktool to remain in firm contact with the culture medium and the specimen as collection occurs. Various ways of applying and maintaining downward force between the picktool and the medium are described below with respect to FIGS. 6-10, for example. Then, as seen at D (FIGS. 1) and 260 (FIG. 2), the actuator can then cause the device to retract the picktool from the specimen surface (the picktool should move vertically upward initially to avoid dragging the picktool across the plate surface) and then move the device to a specimen deposit location, e.g., a sample preparation station, and then cause the collected specimen to be released from the picktool into a solution for further processing.

Afterwards, at E (FIG. 1) the device 100 can be put in the second operational mode and moved to a third station, at which time the device can then discard the used picktool. The process then can start again by causing the device to collect another (unused) picktool at A. The picktool is collected by the device as described above.

Figure 3:
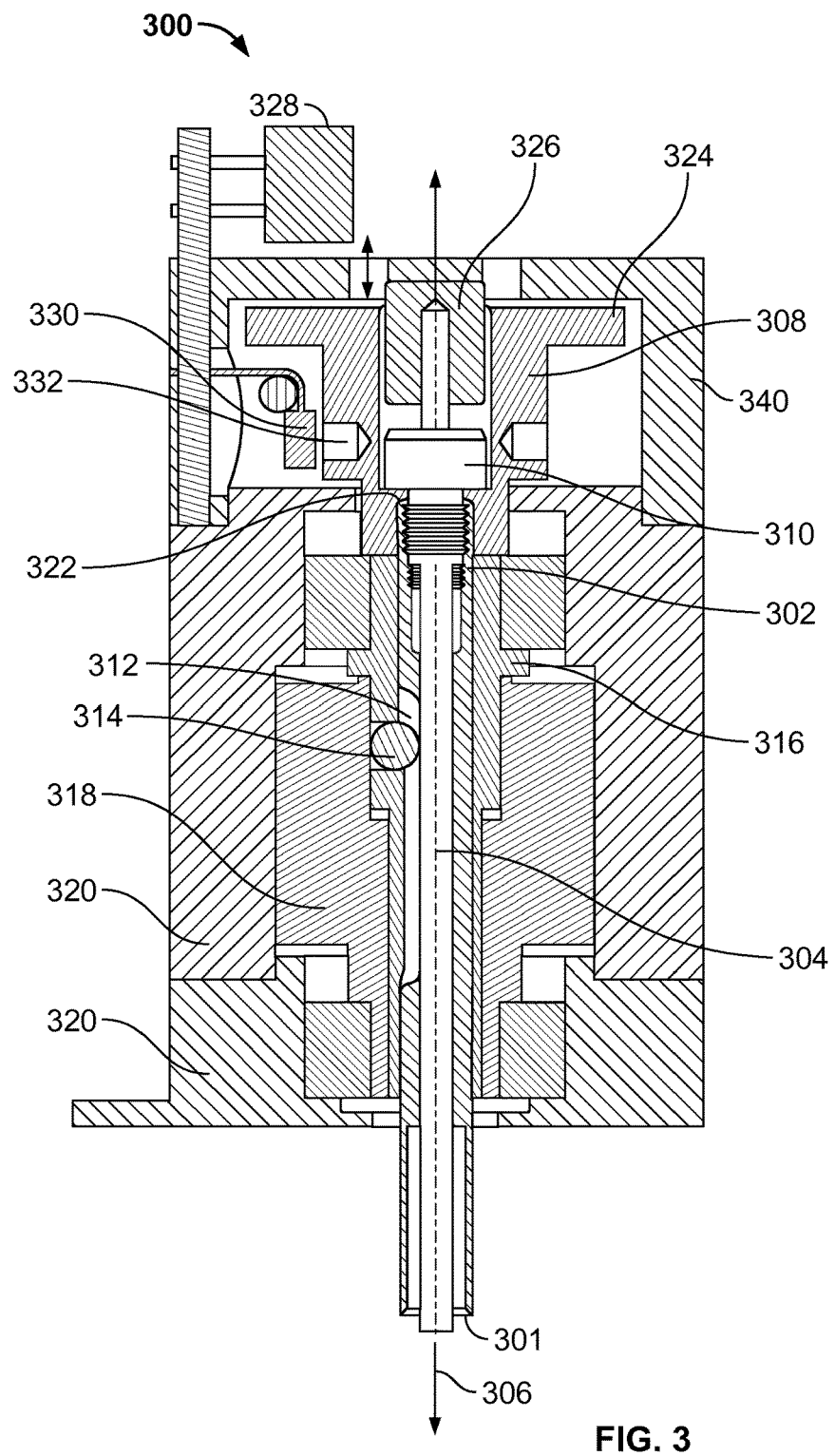
FIG. 3 is a sectional view schematically illustrating a structure of an exemplary device for collecting a specimen from a medium in accordance with an embodiment of the invention.

Referring now to FIG. 3, a specific example will now be provided of a device 300 in accordance with an embodiment of the invention. As illustrated in the FIG. 3 embodiment, device 300 has a picktool-receiving body 302 having a cavity 305 therein for receiving a portion of a picktool 102 (FIG. 1) which can be a shaft of the picktool. One skilled in the art is aware of many different configurations in which the device might be configured to receive a picktool. The invention is not to be construed as limited to the specific configuration illustrated in FIG. 3. The cavity 305 defines an axis 306 extending in an axial direction, in which direction the picktool shaft extends when received in the cavity 305. As received in the cavity 305, the picktool is firmly retained by the body 302 so as to preclude movement relative to the body except at times when the shaft of the picktool is being inserted into the body 302 or being removed or jettisoned therefrom.

The cross-sectional dimension and shape of the cavity 305 typically match the dimension and shape of the shaft of the picktool, but in some cases the dimensions and shapes need only correspond to the extent that the picktool when received is firmly retained in the cavity 305. A rod 304 can be slidably disposed within the body 302, the rod having, for example, a fixed knob 326 which can be forced upward when a picktool is inserted into the open end 301 of the body 302. The rod 304 may be biased to project downwardly to the open end 301 when a picktool is not inserted into the body 302.

As further seen in FIG. 3, an optical reflective sensor 328 may be provided for detecting when the knob 326 is pushed upward, so as to detect the presence of a picktool received by the body 302.

The body 302 may have a threaded hole at a top thereof for mounting a head 308, such as with a screw 309, for example. The body 302 may have a groove 312, typically having a V-shape, in which a bead or ball 314 may be situated and permitted to roll. A sleeve 316 may have a corresponding hole so that the ball is retained between the sleeve and the body 302.

In one example, the sleeve 316 can be press fitted into an opening of a hollow rotor 318 of a motor, such as a stepper motor of the device in which elements 320 represent further portions, e.g., a housing and stator of the motor. The sleeve 316 and picktool receiving body 302 cooperate together to allow the body 302 to move freely in an axial direction, e.g., vertically, which is a direction away from the open end 301 of the body, while locking the body to the rotor 318 of the motor, such that the body 302 can be controllably rotated between various positions by rotating the rotor.

Figure 4A:
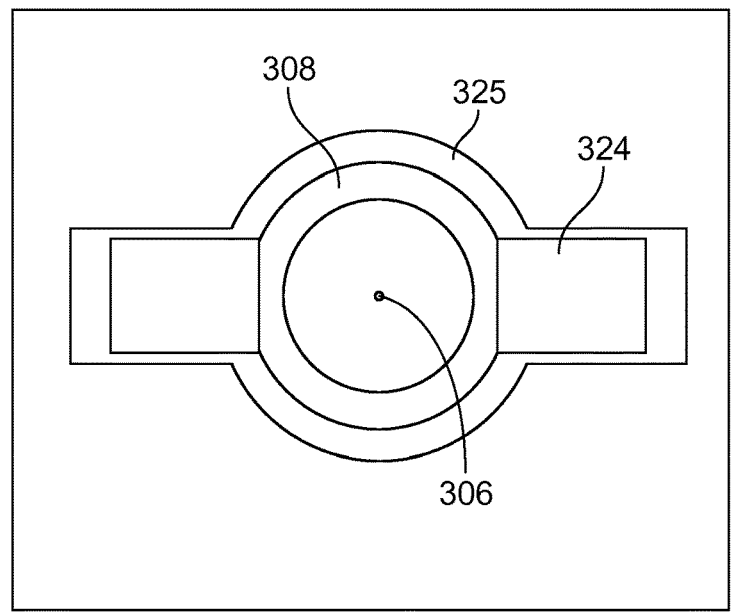
FIG. 4A is a plan view schematically illustrating a device in a first position for operation in a first mode.
Figure 4B:
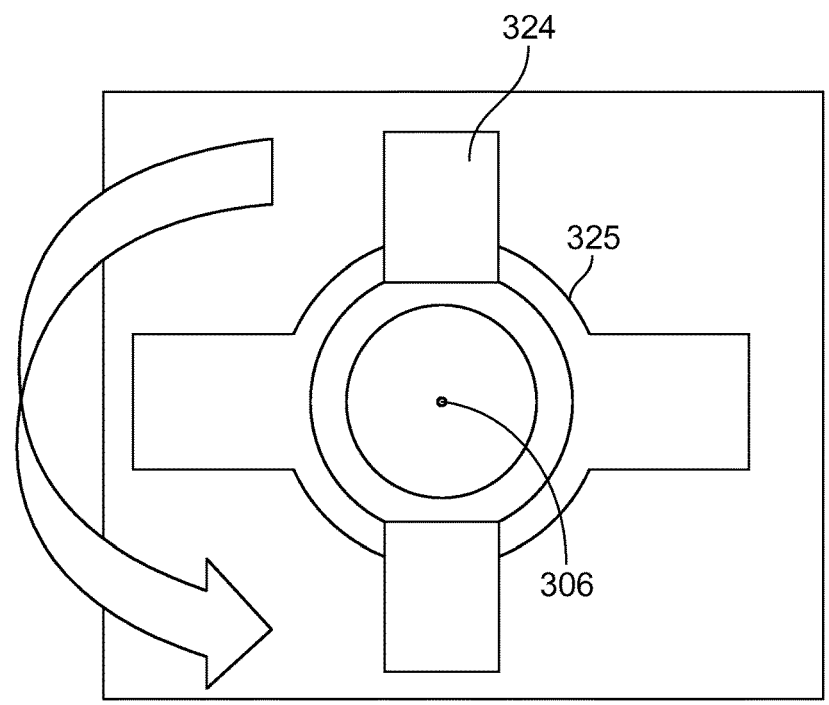
FIG. 4B is a plan view schematically illustrating a device in a second position for operation in a second mode.

The head 308, attached at a top end 322 of the body 302 which is remote from the open end 301, may have one or more portions extending in a lateral direction away from the axis 306. As depicted in FIG. 3, the laterally extending portions may be two wings 324 which extend in opposite directions away from the axis 306. As further shown in plan view in FIG. 4A (looking upward from beneath device structure 340), in the first mode of operation, in a first position, the wings 324 can be aligned with a corresponding opening 325 in the device structure, e.g., a top cover of the device. In this first mode, the alignment of the wings with the opening allows the wings 324 to move freely in the axial direction of the body 302, e.g., upwardly and downwardly. By contrast, in the second mode of operation the head 308 and wings 324 extending therefrom are positioned so that the wings are not aligned with the opening 325, as seen at FIG. 4B. For example, in the second position the head may be rotated to an angle of 90° relative to the first position, such that structure of the device restrains the head 308 and the body 302 attached thereto from moving in the axial directions.

Although the head 308 with wings 324 and opening 325 in FIG. 3 are depicted as a 'keyhole' arrangement, other arrangements are possible which serve the function equally well. For example, instead of the opening having a cylindrical portion and side portions extending in opposite directions away from the axis 306, the opening may alternatively have the shape of a simple rectangle sufficient to accommodate the wings in the first position, while in the second opening the wings are blocked from moving in the axial direction by the area of the structure lying outside of such rectangular opening.

The device may include a detector 330 for generating a signal in response to the picktool contacting the culture medium. In one example, the detector may detect movement of the head in the axial, e.g., upward direction such as when the device moves downwardly towards a medium and the picktool then contacts the medium. Such detector 330 then generates a signal when the body is thrust upward upon contact with the culture medium in a state in which the head 308 and body 302 of the device are in the first position that permits the body to freely move in the axial direction. In one example, the detector may be a Hall effect sensor 330 that is configured to generate an electrical signal in response to a change in magnetic field, such as due to movement of a magnet 332 disposed in or on the head 308. In one example, the head 308 may incorporate four magnets 332 at a periphery of the head, each magnet spaced apart from the next adjacent magnet on the head by a 90 degree angle, wherein the magnetic polarization of the magnet at each position on the head alternates relative to the magnetic polarizations of the magnets adjacent to such magnet at the periphery of the head. The detector and such four magnet arrangement can be used to detect whether the head is aligned with the opening in the first position, or whether the head is in a second position that is rotated about the axis 306 relative to the first position such that the head is then restrained from moving axially. When the head is in a known position, the detector or Hall effect sensor 330 can be used to detect a vertical movement of the head away from the known position.

In an example of operation, when the head 308 is restrained from moving axially by device structure 340, the device 300 can be moved in a downwardly direction by an external actuator (110; FIG. 1) onto the shaft of the picktool 102 to receive the picktool within the body. Downward movement of the device can be continued until the picktool has been inserted to a predetermined position in the body or until the optical sensor 328 detects the knob 326.

Then the device 300 can be moved upwardly by the actuator 110 and the rotor 318 of the stepper motor can be actuated so as to rotate the body through an angle of 90 degrees. At such time, the device is now in a first mode with the head 308 in a first position allowing unblocked vertical movement. The device 300 then is positioned above a surface of the medium containing the specimen (e.g., without limitation a microbial or bacterial colony on a growth medium such as agar), and then moved downward slowly until the detector 330 generates a signal based on the upward movement of the head 308. The actual position of the vertical actuator at the time the signal is generated can be used to determine a height of the device relative to the medium at which the specimen lies on the medium. The picktool may now rest on the specimen, for example, a bacterial colony on a culture medium such as an agar medium, with a downward force which depends on the weight of those components associated with the portions of the device that move axially relative to the other portions of the device (e.g. body 302, rod 304, etc.).

In a particular embodiment, when operating the device in the first mode to detect a surface of the medium, if the total surface pressure of the picktool on the medium is too high (such as due to the combined weight of the device portions bearing down thereon), a magnet coupled with the body 302 can be positioned in a coil. In this way, when the coil is energized, the coil generates a magnetic field which acts on the magnet to create a force that can dampen the pressure of the picktool on the surface of the culture medium.

Figure 5:
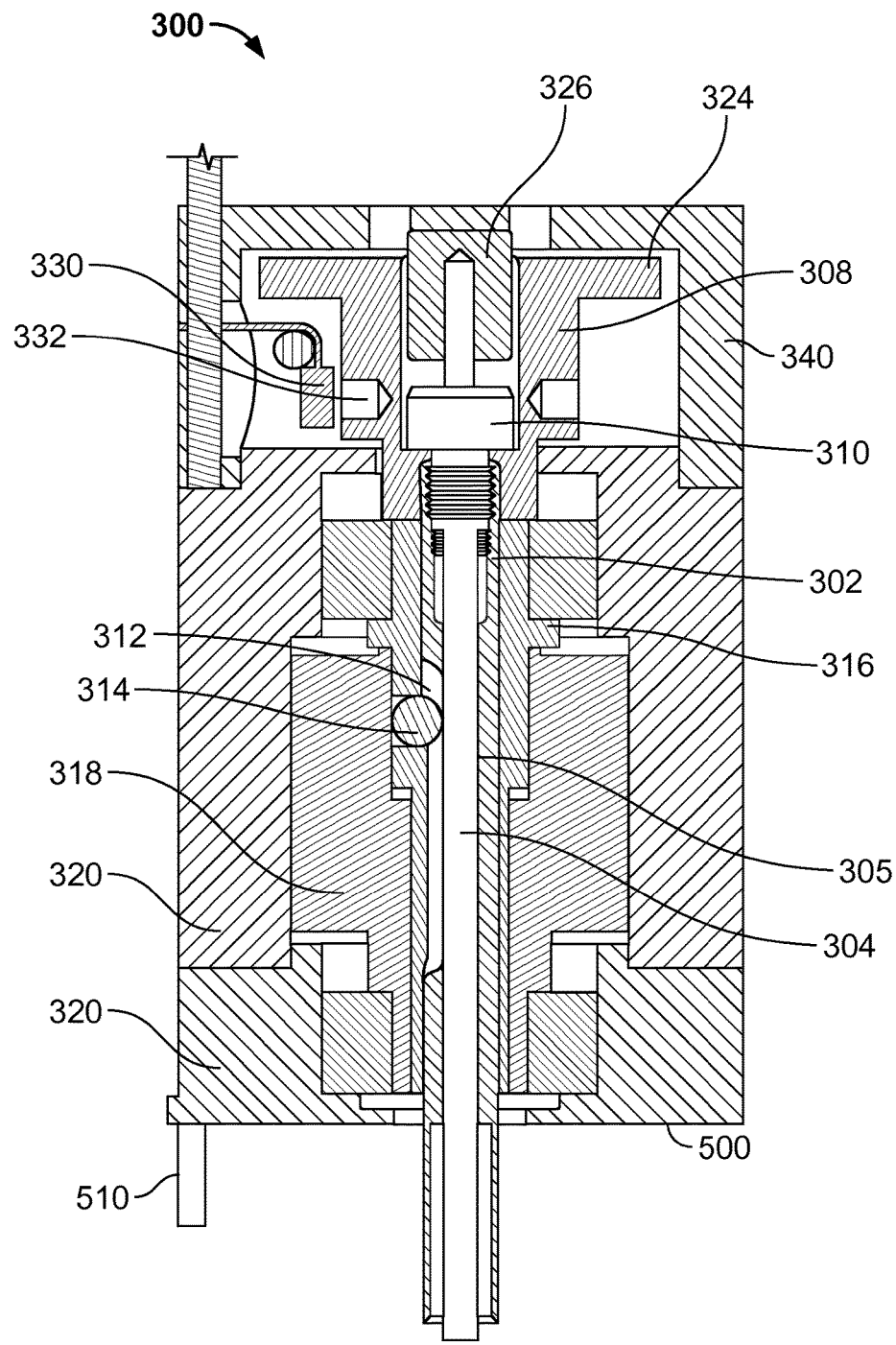
FIG. 5 a sectional view illustrating a variation of the embodiment shown in FIG. 3.
Figure 6:
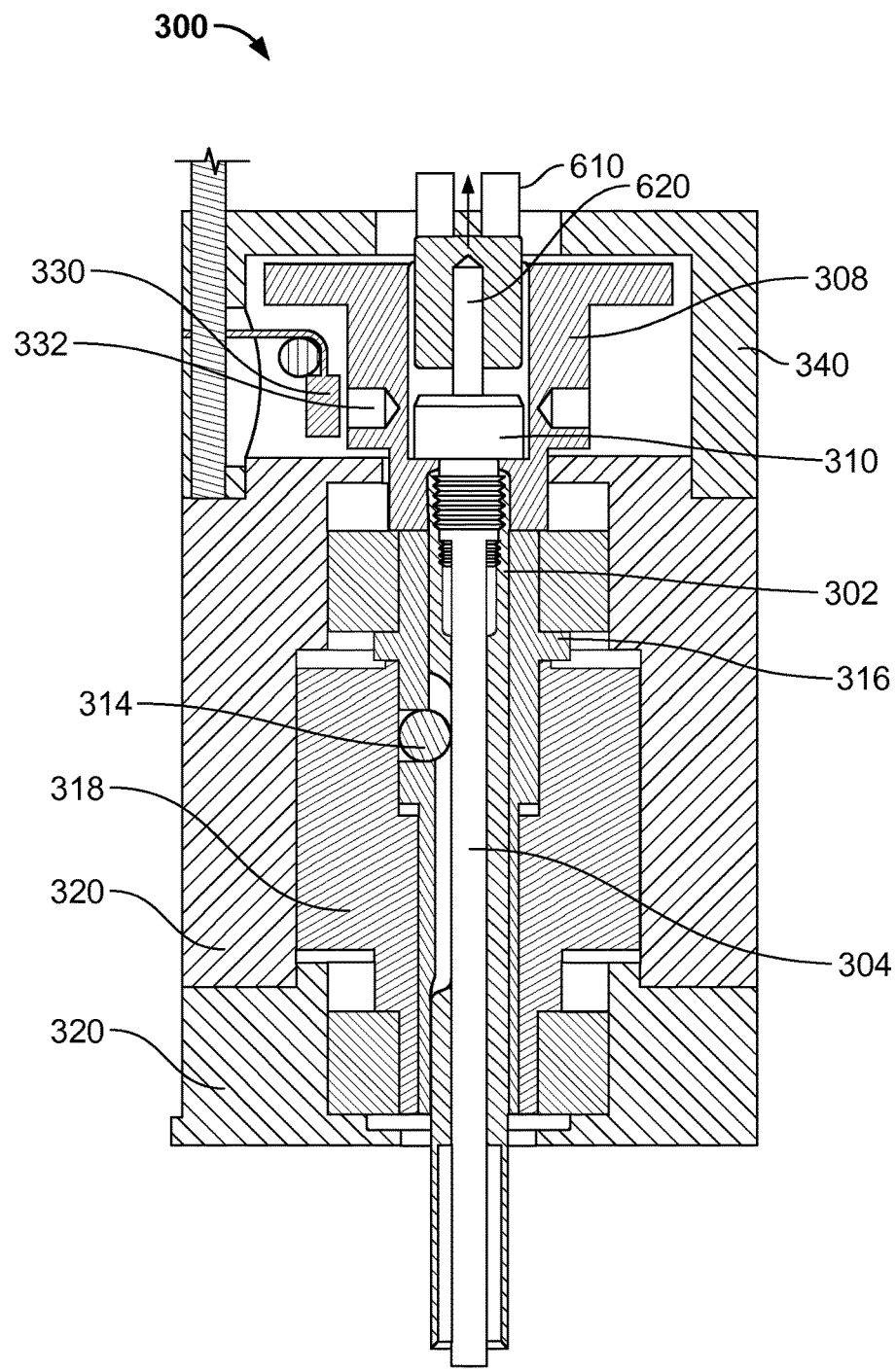
FIG. 6 a sectional view illustrating a variation of the embodiment shown in FIG. 3.

Functions and features of the above-described device can be implemented in a variety of ways. For example, as seen in FIG. 5, alternatively, or in in addition to the sensor 328 (FIG. 3), the device may include an optoelectronic sensor 510 associated with a front surface 500 of the device. The sensor 510 may be configured as a reflective sensor for receiving light reflected from the picktool or from a surface of the culture medium. In one embodiment, the sensor 510 is configured to emit light in a direction towards the picktool and a signal based on a proportion of the emitted light is reflected from a surface of the picktool back on to the sensor. In a particular embodiment, the sensor may be U-shaped. The sensor is positioned so that it can detect the position of the picktool relative to the position of the body 302.

In one embodiment, the device may include an inductive sensor 610 for detecting movement and/or presence of a metal part into proximity with the inductive sensor. For example, the inductive sensor 610 has a structure with which a part 620 (the upper portion of rod 304) associated with the body moves into proximity in response to upward movement of the body 302 when the picktool contacts the surface of the culture medium. In such embodiment, the part 620 is electrically conductive and typically made of metal to permit detection by the inductive sensor 610. In one embodiment the inductive sensor has an annular structure and 'knob' 326 (FIG. 3) is omitted or sized to fit within the opening in the inductive sensor. In a variation of such embodiment, the inductive sensor may be provided as one or more inductive coils.

Alternatively, in one embodiment, the device may include one or more capacitive sensors which are capable of detecting presence of either metal or non-metal parts. The one or more capacitive sensors can be provided in place of inductive sensor 610. In such embodiment, the capacitive sensor can detect the presence of or movement of a part 620 of the device, whether or not the part 620 is made of metal. In this embodiment, the sensor is a variable capacitor, capacitance varying with the position of the rod. A change in capacitance will indicate upward force caused by contact of the picktool with the specimen, for example.

Figure 7:
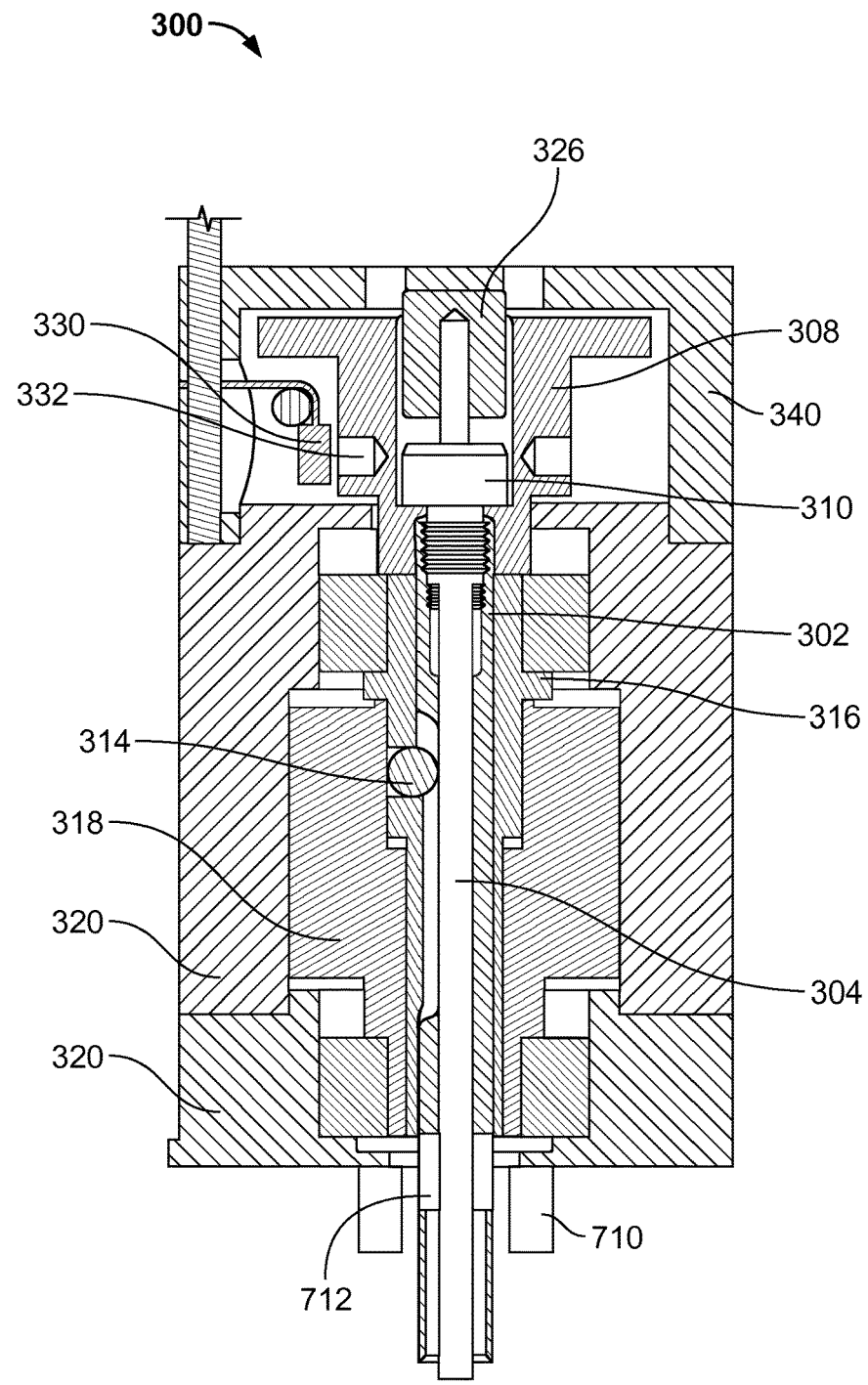
FIG. 7 a sectional view illustrating a variation of the embodiment shown in FIG. 3.
Figure 8:
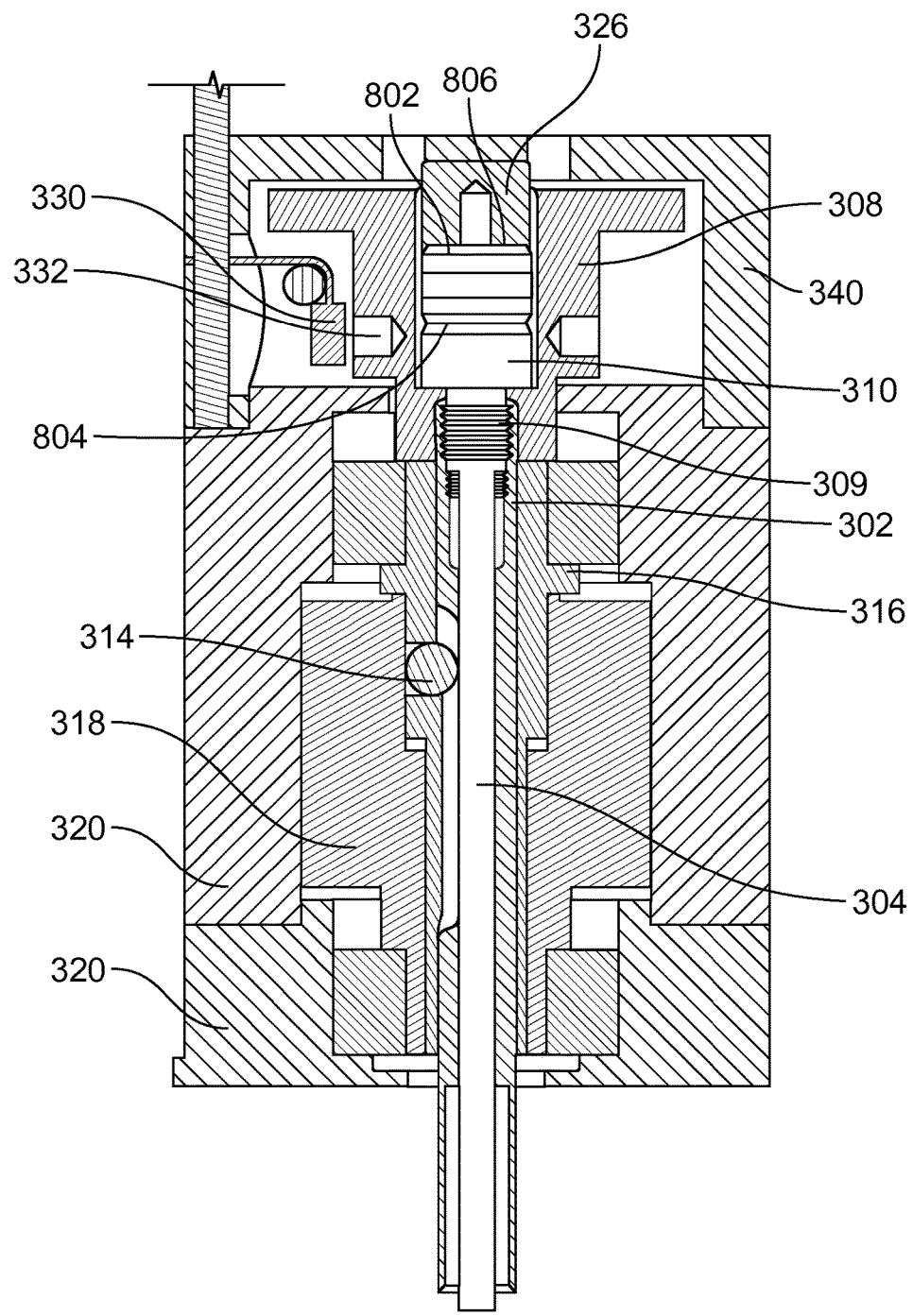
FIG. 8 a sectional view illustrating a variation of the embodiment shown in FIG. 3.

Particular embodiments of the device can include structure configured to increase downforce between the picktool and the culture medium, such as for when the picktool is in contact with the culture medium for collecting a specimen. For example, FIG. 7 depicts an inductive coil 710 which can be used in conjunction with one or more magnets 712 or magnetic portions of the body 302. The magnetic coil can be configured to add resistance to the axial motion of the body 302 or repel the body 302 in the axial direction. In the second instance, the coil may be energized with a first applied current to apply a magnetic attractive force to the magnets 712 to cause the magnets to be attracted towards the coil 710 and apply a downward force to the body 302 to move the body downwards. When the coil is energized at a lower current level or is not energized, the coil applies less force to the body 302 and the body may then move upwards with less or no resistance. The device may additionally include a restoring element, which may be, for example, a spring (802; FIG. 8), the restoring element configured to restore a position of the body 302 to a resting position when the coil is energized at a lower level or when the coil is not energized.

In one embodiment, the coil may be configured to be energized with current of opposite polarity from the first applied current. In this case, the coil applies a magnetic repulsive force to the magnets 712 to cause the magnets to be repulsed away from the coil 710 to apply an upward force to the body 302.

FIG. 8 illustrates an embodiment which includes a spring 802 for providing a restoring force to the body 302. In the illustrated embodiment the spring is disposed above the body providing increased resistance to the body moving upwards. In one example, the spring 802 has a first end 804 mechanically coupled with the body 302 such as through screw 309 with screwhead 310, and a second end 806 abutting a part of the device having a fixed position. In operation, movement of the body 302 in the upward direction compresses the spring 802, such that the spring applies increased downforce on the body 302 which downforce increases the more the body moves upward. In such way, the device applies an increased force between the picktool and the culture medium when the picktool is forced into contact with the culture medium.

Figure 9:
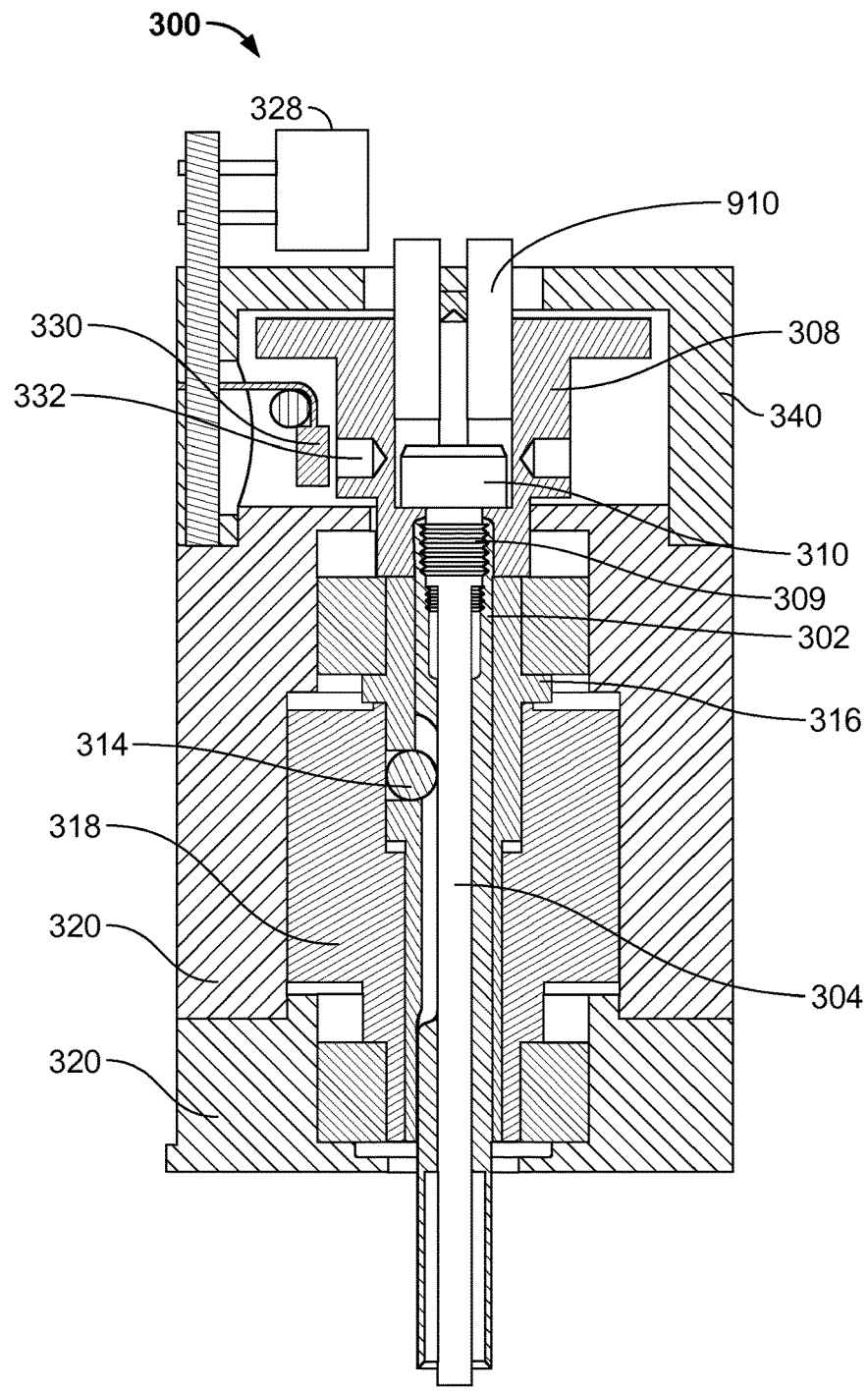
FIG. 9 a sectional view illustrating a variation of the embodiment shown in FIG. 3.

In one embodiment as seen in FIG. 9, the device may include one or more weights 910 which are arranged to apply an increased downward gravitational force on the body 302 after the body has moved a predetermined upward distance from a resting position of the body 302. For example, an annular weight 910 can be positioned so as to rest partly on a ledge (not shown) on or within the device. When the device is moved by the actuator downwardly towards the culture medium, the body 302 moves upward upon contact with the culture medium, such that an element, e.g., screwhead 310 coupled with the body, eventually comes into contact with the weight 910. If the body remains at the same position or continues to move upwardly, the weight 910 is now coupled with the body 302 so as to apply a downward gravitational force through the body 302 to the culture medium.

Figure 10:
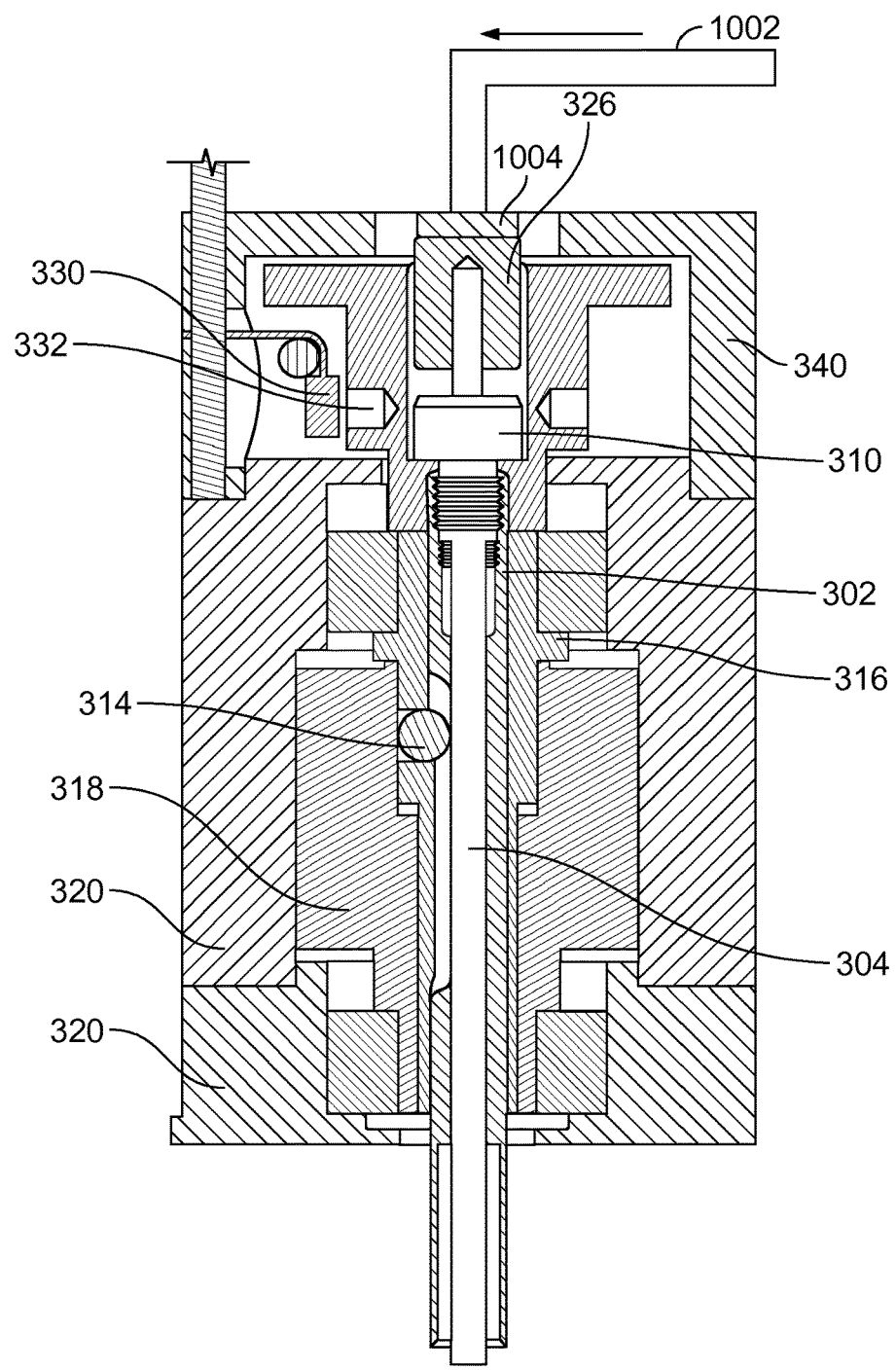
FIG. 10 a sectional view illustrating a variation of the embodiment shown in FIG. 3.

In another embodiment as seen in FIG. 10, pressurized air or gas within a sealed chamber 1004 can apply downforce to the body 302 when the body is moved into contact with a culture medium. Thus, when the device is moved by the actuator downwardly towards the culture medium, the body 302 moves upward upon contact with the culture medium, such that an element (knob 326) moving within the chamber 1004 compresses the gas inside. As the gas compresses, the gas applies an increasingly greater force to the knob 326. In such way, the gas within chamber 1004 acts as a passive restoring element applying increased force on the body when the body is in contact with the culture medium. In such case, the chamber 1004 is thoroughly sealed, with seals provided between the knob 326 and a wall of the chamber, such that air or gas neither enters nor escapes from the chamber 1004.

In a variation of such embodiment, the device may further include a conduit 1002 connected to a pump, tank or regulator device for supplying or withdrawing gas from the chamber 1004. In such case, gas can be actively supplied to the chamber when increased downforce is to be applied to the body. In a particular example, gas can be withdrawn from the chamber through the conduit to apply reduced force to the body or to move the body upwards.

Although the above-described embodiments refer to use of a consumable picktool that is received by the device and used to collect a specimen after which the picktool is discarded, the principles and embodiments of the invention can apply also to devices in which the picktool remains an integral part of the device for the repeated collection of specimens, and the picktool is generally not discarded unless damaged or worn.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for collecting a specimen from a culture medium, comprising:
   a body comprising a cavity structure for receiving a replaceable picktool, the body and picktool being in approximately axial alignment; and
   a detector configured to generate a signal in response to a force applied to the picktool when the picktool is brought into contact with a specimen disposed on a culture medium,
   wherein the device is configured to operate in at least first and second modes, wherein the first mode permits the body and the picktool to move freely in an axial direction, which is proximately perpendicular to a surface of the culture medium, and the second mode applies more resistance to the axial movement of the body and the picktool than when the device is in the first mode;

wherein the device further comprises a device structure coupled to the body, wherein the body moves more freely in the axial direction relative to the device structure in the first mode, and the body is locked from such axial movement in the axial direction in the second mode and a key coupled to the body, wherein the key cooperates with an opening in the device structure above the key so that the key does not engage and may advance into and through the device structure in the first mode and in which the key cannot advance into and through the device structure in the second mode.

2. The device of claim 1, wherein an amount of the resistance in the second mode progressively increases with displacement of the body beyond a first predetermined range of motion.

3. The device of claim 2, wherein an amount of the resistance in the second mode increases as a step function upon displacement of the body beyond the first predetermined range of motion.

4. The device of claim 3, further comprising a spring configured to begin to resist axial movement of the body in response to movement of the body at or following contact between the picktool and the specimen disposed on the culture medium when the device switches to the second mode.

5. The device of claim 1, wherein the detector is configured to generate a signal in response to detecting a relative position between the device and the specimen.

6. The device of claim 1, wherein the device is configured to switch from the first mode to the second mode when the picktool is in contact with or comes into contact with the specimen disposed on the culture medium.

7. The device as claimed in claim 1, further comprising a motor coupled to the body for rotating the body in a direction about the axis, the motor being configured to rotate the body relative to the device structure between a first position corresponding to the first mode in which the key can advance into and through the device structure and a second position corresponding to the second mode in which the key cannot advance into and through the device structure.

8. The device as claimed in claim 1, wherein the key comprises at least one lateral extension away from an axis common to the key and the body, and the opening is sized to permit the at least one lateral extension to pass therethrough.

9. The device of claim 1, further comprising a sleeve through which the body extends, wherein in the first mode the body is freely moveable in the axial direction within the sleeve and the sleeve restrains the body in coaxial arrangement therewith, and in the second mode the sleeve and the device structure cooperate to restrain movement of the body relative to the device structure.

10. A method for collecting a specimen from a culture medium comprising:
  initiating the first mode of the device of claim 1 for collecting a specimen from a culture medium, the first mode permitting movement of the device in the axial direction relative to a support structure of the device;
  moving the device in the axial direction to receive and retain the picktool configured to collect the specimen;
  moving the picktool, by the device, into contact with the specimen disposed on the culture medium;
  initiating the second mode of the device and precluding movement of the device in the axial direction;
  manipulating the picktool while the picktool is attached to the device to collect the specimen; and
  depositing the collected specimen at a collection location.

11. The method of claim 10, further comprising after depositing the collected specimen, processing the collected specimen, the step of processing including at least one of the processes selected from the group comprising processing testing, culturing, or preserving.

12. The method of claim 10, wherein the step of manipulating includes the device rotating the picktool.

13. The method of claim 10, further comprising releasing the picktool from the device so as to discard the picktool.

14. The method of claim 10, further comprising detecting contact between the picktool and the culture medium.

15. The method of claim 14, further comprising detecting a height at which the picktool contacts the culture medium.

16. The method of claim 10, further comprising determining a height at which the picktool contacts the specimen.

* * * * *